United States Patent [19]
Kappock et al.

[11] Patent Number: 6,096,122
[45] Date of Patent: *Aug. 1, 2000

[54] DISCOLORATION PREVENTION IN PYRITHIONE-CONTAINING COATING COMPOSITIONS

[75] Inventors: Paul S. Kappock, E. Hampton; Craig Waldron, Waterbury, both of Conn.

[73] Assignee: Arch Chemicals, Inc., Norwalk, Conn.

[ * ] Notice: This patent is subject to a terminal disclaimer.

[21] Appl. No.: 09/212,877

[22] Filed: Dec. 16, 1998

Related U.S. Application Data

[62] Division of application No. 08/670,051, Jun. 25, 1996, Pat. No. 5,883,154, which is a division of application No. 08/383,122, Feb. 3, 1995, Pat. No. 5,562,995.

[51] Int. Cl.$^7$ .............................. C09D 5/16; C09K 15/04
[52] U.S. Cl. .................................. 106/18.36; 106/18.33; 106/15.05; 252/400.52; 252/405; 523/122
[58] Field of Search .............................. 106/18.36, 18.33, 106/15.05; 252/400.52, 405, 406, 397; 523/122, 99

[56] References Cited

U.S. PATENT DOCUMENTS

| | | |
|---|---|---|
| 2,809,971 | 10/1957 | Bernstein et al. . |
| 3,159,640 | 12/1964 | McClure et al. . |
| 4,396,766 | 8/1983 | Farmer, Jr. et al. . |
| 4,482,715 | 11/1984 | Trotz et al. . |
| 4,675,375 | 6/1987 | Kempter et al. ........................ 528/140 |
| 4,818,436 | 4/1989 | French et al. . |
| 4,888,368 | 12/1989 | Kohl et al. . |
| 4,957,658 | 9/1990 | French et al. . |
| 5,227,156 | 7/1993 | Wiese . |
| 5,232,493 | 8/1993 | Waldron et al. . |
| 5,246,489 | 9/1993 | Farmer, Jr. et al. ................. 106/18.33 |
| 5,342,437 | 8/1994 | Gavin et al. . |
| 5,518,774 | 5/1996 | Kappock et al. ........................ 427/384 |

*Primary Examiner*—Terrel Morris
*Assistant Examiner*—Cheryl Juska
*Attorney, Agent, or Firm*—Dale L. Carlsons; Wiggin & Dana

[57] ABSTRACT

Disclosed is a process for inhibiting the formation of discoloration in an aqueous composition selected from the group consisting of water-based paint, adhesive, caulk and sealant compositions, and combinations thereof, wherein said discoloration is caused by the presence of ferric ion or cupric ion together with pyrithione in said composition. The process comprises contacting the composition with a discoloration-inhibiting amount of a zinc compound selected from the group consisting of zinc salts of organic acids, zinc salts of inorganic acids, zinc hydroxide, zinc oxide, and combinations thereof. Also disclosed is an aqueous antimicrobial composition protected against discoloration attributable to the presence of ferric ion or cupric ion therein.

3 Claims, No Drawings

DISCOLORATION PREVENTION IN PYRITHIONE-CONTAINING COATING COMPOSITIONS

CROSS-REFERENCE TO RELATED APPLICATION

This is a divisional application of U.S. application Ser. No. 08/670,051, that was filed on Jun. 25, 1996, now U.S. Pat. No. 5,883,154, and is incorporated herein by reference in its entirety, which, in turn is a divisional application of U.S. application Ser. No. 08/383,122, filed on Feb. 3, 1995, now U.S. Pat. No. 5,562,995, also incorporated herein by reference in its entirety.

FIELD OF THE INVENTION

This invention relates generally to coating compositions, and, more specifically, to methodology for preventing or reducing discoloration in pyrithione-containing coating compositions.

BACKGROUND OF THE INVENTION

Sodium pyrithione (also called the sodium salt of 1-hydroxy-2-pyridinethione, sodium pyridine-2-thiol-N-oxide, or 2-pyridinethiol-1-oxide, Na salt) has excellent antimicrobial properties, and is typically employed as a biocide and preservative in functional fluids, such as metalworking fluids, lubricants, cosmetics and toiletries. Sodium pyrithione is a well-known commercial product commonly made by reacting 2-chloropyridine-N-oxide with NaSH and NaOH, as disclosed, for example, in U.S. Pat. No. 3,159,640.

Likewise, zinc pyrithione [also known as zinc pyridine-2-thiol-N-oxide or bis [1-hydroxy-2(H) pyridinethionato]-zinc] is an excellent antimicrobial additive. Zinc pyrithione may be made by reacting 1-hydroxy-2-pyridinethione or a soluble salt thereof with a zinc salt (e.g., $ZnSO_4$) to form a zinc pyrithione precipitate, as disclosed, for example in U.S. Pat. No. 2,809,971. Zinc pyrithione has been employed as a broad-spectrum anti-microbial agent and preservative in metalworking fluids, plastics, paints, adhesives and cosmetics. Its principal uses are as an anti-dandruff agent in hair products, as a preservative in various cosmetics, and as an antifoulant in marine paints. The commercial use of zinc pyrithione in paints, adhesives, caulks and sealants is growing.

In the presence of ferric ion, sodium or zinc pyrithione-containing compositions tend to turn blue even though the ferric ion is present in mere trace amounts. This blue discoloration is undesirable for aesthetic reasons, as well as for functional reasons relating to unwanted color formulation.

More specifically, since the aesthetics of paints, adhesives, caulks and sealants normally require certain desirable colors, and since the formulators of such products go to great lengths to achieve specific color effects, any ingredient which causes the formulation to vary much from a desired white or colorless (i.e., "water white") hue may make the colorant formulators' task very difficult. More specifically, when attempting to utilize pyrithione as an antimicrobial agent in fully-formulated water-based paints, paint bases (i.e., the partially formulated paint before pigment addition), adhesives, caulks and sealants, an unwanted color in an additive can adversely affect the color of the formulated product. Thus, the discoloration typically adversely affects the desired color, producing an off-color product.

In addition to the aesthetics problems and colorant functioning problems, the blue coloration problem associated with the presence of ferric ion causes a performance problem in the sodium pyrithione-containing compositions. This performance problem when using sodium pyrithione results from the fact that the pyrithione tends to form a blue precipitate in the presence of ferric ion. The precipitate reduces the amount of available pyrithione throughout the composition, thereby diminishing the biocidal protection thereof.

In the past, various solutions to the blue discoloration problem have been proposed. By way of illustration, U.S. Pat. Nos. 4,957,658 and 4,818,436 disclose solutions to the above-discussed discoloration problem attributable to the presence of ferric ion plus pyrithione, in paints and functional fluids (e.g., metalworking fluids) respectively, by adding to the paint or functional fluid an alkali metal or alkaline earth metal salt of 1-hydroxyethane-1,1-diphosphonic acid. Although the '658 and '436 patents propose good solutions to the discoloration, these solutions are not always as cost effective or permanent as might be desired.

As another illustration, U.S. Pat. No. 4,161,526 discloses a white to cream yellow pyrithione, pyrithione salt or dipyrithione for application to skin or hair containing from about 0.01 percent to about 1 percent of the zinc salt of an organic carboxylic or inorganic acid, zinc hydroxide or zinc oxide, or a mixture thereof. The composition of the '526 patent is said to be effective in preventing or removing discoloration caused by formation of a colored pyrithione, pyrithione salt, or dipyrithione contaminant (said to be iron pyrithione) in the composition. Unfortunately, the '526 patent does not teach a solution to the discoloration problem in compositions unrelated to skin or hair care, and not containing iron pyrithione. Furthermore, the '526 patent teaches the use of higher levels of the zinc salt, zinc oxide or zinc hydroxide than otherwise might be desired.

New solutions to the blue and green discoloration problem in various aqueous compositions, particularly paints, adhesives, caulks and sealants which enables pyrithione to be utilized therein in the presence of iron or copper, without any resulting discoloration of the composition, and that is cheaper, longer lasting, and/or uses lower levels of additives than required by the above-discussed prior art, would be highly desired by the paint, adhesives, caulks and sealants manufacturing community. The present invention provides one such solution.

SUMMARY OF THE INVENTION

In one aspect, the present invention relates to a process for inhibiting the formation of discoloration (e.g., a blue, grey, or green off-color formation) in an aqueous composition selected from the group consisting of water-based paint, adhesive, caulk and sealant compositions, and combinations thereof, wherein said discoloration is caused by the presence of ferric ion or cupric ion together with pyrithione in said composition, which comprises contacting the composition with a discoloration-inhibiting amount (advantageously between 10 ppm and 90 ppm, more advantageously between 10 ppm and 70 ppm, based upon the weight of the composition) of a zinc compound selected from the group consisting of zinc salts of organic acids (e.g., zinc acetate), zinc salts of inorganic acids (e.g., zinc sulfate and zinc chloride), zinc hydroxide, zinc oxide, and combinations thereof.

In another aspect, the present invention relates to a process for removing an undesirable discoloration in an aqueous antimicrobial composition containing a dissolved metal ion selected from the group consisting of ferric ion, cupric ion, and combinations thereof, and containing pyrithione (preferably in an antimicrobially effective amount), which comprises contacting said composition with a zinc ion in a molar amount at least equal to the amount of said dissolved metal ion in said composition. Advantageously, the zinc ion is present in the composition in an amount of between 10 ppm and 90 ppm, more advantageously between 10 ppm and 70 ppm, based upon the weight of the composition.

In yet another aspect, the present invention relates to an aqueous antimicrobial composition, protected against discoloration attributable to the presence of ferric ion or cupric ion therein, said composition being selected from the group consisting of water-based paints, adhesives, caulks and sealants, and combinations thereof, said composition comprising water, an organic base medium and zinc ion, said zinc ion being present in said composition in an amount of between 10 ppm and 90 ppm, more advantageously between 10 ppm and 70 ppm. The zinc ion is suitably provided in said composition by the incorporation therein of a zinc salt of an organic acid or inorganic acid, zinc hydroxide, zinc oxide, or a combination thereof in order to provide the desired amount of zinc ion.

In still another aspect, the present invention relates to a coated substrate comprising a substrate selected from the group consisting of ferrous metal-containing substrates, copper-containing substrates, and combinations, and a coating on said substrate, said coating comprising pyrithione and a zinc compound selected from the group consisting of zinc salts of organic acids (e.g., zinc acetate), zinc salts of inorganic acids (e.g., zinc sulfate and zinc chloride), zinc hydroxide, zinc oxide, and combinations thereof. Advantageously, the zinc compound is present in said coating in an amount of between 10 ppm and 90 ppm, more advantageously between 10 ppm and 70 ppm, based upon the weight of the coating.

These and other aspects will become apparent upon reading the following detailed description of the invention.

DETAILED DESCRIPTION OF THE INVENTION

It has now been surprisingly found in accordance with the present invention that the addition of zinc to a composition containing pyrithione and ferric or cupric ion reduces or avoids a discoloration problem otherwise attributable to such composition. Without wishing to be bound by any particular theory, the discoloration problem is believed to be caused by the formation of an insoluble iron pyrithione precipitate that not only discolors the composition, but also depletes the available pyrithione in sodium pyrithione-containing compositions, thereby diminishing the antimicrobial efficacy of the composition.

The term "discoloration" as employed herein with respect to pyrithione-containing compositions that also contain ferric ion or cupric ion dissolved therein is intended to describe any unacceptable gray, blue, black, purple, green, or color other than the natural color or desired artificial color of the paint or paint base formulation. Starting materials employed in preparing the aqueous compositions of the present invention typically include tap water, as well as a source of pyrithione in the form of sodium pyrithione, zinc pyrithione, and combinations thereof. It is noted, for example, that the natural color of sodium pyrithione itself is a clear yellow. It is quite common, however, for iron and/or copper contaminants to be introduced into the aqueous composition from the tap water used, causing discoloration of the composition. One way of quantifying the discoloration is by measuring the reflectance color parameters, and calculating a whiteness value from them. Another method is to visually inspect the composition for any signs of off-whiteness, as compared to the desired or white color.

In water-based paints, adhesives, caulks and sealants a level of ferric or copper ion of 10 ppm or higher is not uncommon. By incorporating an effective amount of the zinc salt of an organic acid or inorganic acid, zinc hydroxide or zinc oxide or a mixture thereof into the composition, the blue discoloration typically attributable to the presence of ferric ion bound with pyrithione is suitably reduced, eliminated or avoided, as is the green discoloration attributable to the presence of copper ion.

Although the amount of the above described zinc salt of an organic acid or inorganic acid, zinc hydroxide or zinc oxide, or combination thereof, needed to prevent discoloration in the aqueous composition in which it is employed can vary over a wide range of between 0.001% or lower to 10% or greater, based upon the weight of the aqueous composition in which it is employed, it has been surprisingly found in accordance with the present invention that the discoloration associated with tap water contamination by iron or copper is suitably reduced or avoided by incorporating into said composition an amount of between 10 ppm and 90 ppm, more advantageously between 10 ppm and 70 ppm, of the zinc ion. Although not wishing to be bound by any particular theory, the present inventors believe that the efficacy of such low levels of zinc ion in resolving the discoloration problem is attributable to a "common ion effect" forcing an equilibrium toward unionized zinc pyrithione where zinc ion, pyrithione ion, and unionized zinc pyrithione are all present in the composition.

The pyrithione used in the process and composition of this invention is preferably a pyrithione salt, such as sodium pyrithione, zinc pyrithione, chitosan pyrithione, magnesium disulfide pyrithione, and the like, although pyrithione acid can be used if desired. More preferable pyrithione salts include sodium pyrithione, and zinc pyrithione, most preferably zinc pyrithione.

The sodium pyrithione useful in the present invention is a well-known commercial product that is commonly made by reacting 2-chloropyridine-N-oxide with NaSH and NaOH, as illustrated by the disclosures of U.S. Pat. No. 3,159,640.

Zinc pyrithione may be made by reacting 1-hydroxy-2-pyridinethione (i.e., pyrithione acid) or a soluble salt thereof with a zinc salt (e.g., $ZnSO_4$) to form a zinc pyrithione precipitate, as illustrated by the disclosures of U.S. Pat. No. 2,809,971.

The aqueous compositions of the present invention are suitable for a variety of uses, such as, for example as soap, shampoo, skin care medicaments, paint, or incorporated into or onto plastic or a woven or non-woven fibers, when formulated to contain the requisite components in addition to the antimicrobial component.

The antimicrobial compositions of the present invention are particularly useful in the form of paints, including indoor and outdoor household paints, industrial and commercial paints. Particularly advantageous results are obtained when the compositions of the present invention are utilized as marine paints for use, for example, on ship's hulls. In addition, the antimicrobial compositions provide desirable results when the antimicrobial component is incorporated into exterior paints of the latex and alkyd types. The antimicrobial component of the aqueous composition is also useful as an "in-can" preservative during storage and prior to use of the paint.

Typically a paint composition will contain, in addition to the antimicrobial component, a resin, a pigment, and various optional additives such as thickening agent(s), wetting agents and the like, as is well known in the art. The resin is preferably selected from the group consisting of vinyl, alkyd, epoxy, acrylic, polyurethane and polyester resins, and combinations of thereof. The resin is preferably employed in an amount of between about 20% and about 80% based upon the weight of the paint or paint base.

In addition, the paint composition of the present invention optionally additionally contains optional additives which have a favorable influence on the viscosity, the wetting power and the dispersibility, as well as on the stability to freezing and electrolytes and on the foaming properties. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally occurring or synthetic clays, such as kaolin, montomorillonite, and bentonite), clay mica (muscovite), and chlorite (hectonite), and the like. In addition to clays other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative, thickening agents include cellulose 30 derivatives, for example methyl, hydroxyethyl, hydroxypropyl and carboxymethyl cellulose, poly(vinyl alcohol), poly(vinylpyrolidone), poly(ethyleneglycol), salts of poly(acrylic acid) and salts of acrylic acid/acrylamide copolymers.

Suitable wetting and dispersing agents include sodium polyphosphate, salts of low molecular weight poly(acrylic acid), salts of poly(ethane sulfonic acid), salts of poly (vinyl phosphonic acid), salts of poly(maleic acid) and salts of copolymers of maleic acid with ethylene, 1 olefins 3 to 18 carbon atoms and/or styrene.

In order to increase the stability to freezing and electrolytes there may be added to the paint composition various monomer 1.2-diols for example glycol, propylene glycol (1.2) and butylene glycol 1.2) or polymers thereof, or ethoxylated compounds. For example reaction products of ethylene oxide with long-chain alkanols, amines, alkyd phenols, poly(propyleneglycol), or poly(butylene glycol), or a combination thereof, or the like.

The minimum temperature of film formation (white point) of the paint composition may be reduced by adding solvents, such as ethylene glycol, butyl glycol, ethyl glycol acetate, ethyl diglycol acetate, butyl diglycol acetate, benzene or alkylated aromatic hydrocarbons. As defoaming agents there are suitable for example poly(propylene glycol) and polysiloxanes. Optionally other biocides can additionally be incorporated into the paint formulations of the present invention. Useful optional solvents include methylisobutylketone (herein referred to as "MIBK"), xylene, ethyl benzene, methanol, and combinations thereof.

The paint composition of the present invention may be used as a paint for natural or synthetic materials, for example wood, paper, metals, textiles and plastics. It is particularly suitable as an outdoor paint, and is excellent for use as a marine paint.

Another significant use for the aqueous composition of the present invention is as a latex tile adhesive typically containing, for example, in addition to the antimicrobial component, a latex emulsion, an optional rosin emulsion, an optional plasticizer, an optional antioxidant, and an optional pigment or filler (such as calcium carbonate). Yet another significant use for the aqueous composition of the present invention is as a latex caulk, typically containing, in addition to the antimicrobial component, an acrylic latex, a nonionic surfactant, a dispersant, an optional plasticizer, and an optional pigment or filler (such as calcium carbonate).

The aqueous antimicrobial compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

The invention is further illustrated by the following Examples. Unless otherwise stated, the "parts" and "%" are "parts by weight" and "percent by weight", respectively.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

The following examples are intended to illustrate, but in no way limit the scope of, the present invention.

EXAMPLE 1

Elimination of Blue Discoloration Caused by the Presence of Pyrithione and Ferric Ion In a Paint Base Efficacy of zinc oxide in eliminating blue coloration caused by the presence of ferric ion in sodium pyrithione containing paint bases.

In order to test the effectiveness of zinc oxide in eliminating or reducing blue color caused by ferric ion in a pyrithione-containing paint, the following experiment was conducted.

Two samples weighing 150 grams each of below aqueous (latex) paint formulation containing sodium pyrithione and zinc oxide were placed in plastic cups. A wooden tongue depressor was then dipped into each sample and then allowed to dry to provide a control or "blank" comparison. Ferric chloride was then added to each sample to provide a concentration of 64 ppm of ferric ion in each sample. Tongue depressor coatings were taken to provide a basis for comparison. No discoloration formed in the paints themselves or the dry films of the painted tongue depressor.

Latex Paint Formulation Containing Sodium Pyrithione and Zinc Oxide:

| Ingredient | Grams |
| --- | --- |
| water | 240.00 |
| hydroxyethyl cellulose | 6.0 |
| Tamol 850[1] | 14.2 |
| Ethylene Glycol | 50.0 |
| Colloid 643[2] | 2.0 |
| Triton ® CF-10[3] | 5.0 |
| sodium pyrithione 40% active | 3.0 |
| potassium tripolyphosphate | 3.0 |
| Pigment grind: | |
| titanium dioxide (Rutile) | 424.0 |
| aluminum magnesium silicate | 228.0 |
| attapulgite clay | 3.0 |
| zinc oxide | 50.0 |
| aluminum silicate | 100.0 |
| propylene glycol | 68.0 |
| Let Down: | |
| water | 84.0 |
| acrylic latex emulsion 58.0% solids | 700.0 |
| Colloid 643 | 6.0 |
| Texanol ®[4] | 18.6 |
| hydroxyethyl cellulose 2.5% in water | 236.4 |
| Total Mass in Grams | 2243.2 |

[1] An anionic dispersant, a product of Rohm and Haas Company
[2] A defoamer, a product of Rhone-Poulence Corp.
[3] A nonionic surfactant, a product of Union Carbide Corp.
[4] A coalescent, a product of Eastman Kodak Company Next, as a comparison, two samples weighing 150 grams each of below aqueous (latex) paint formulation containing sodium Pyrithione and no zinc oxide were placed in paper cups. A wooden tongue depressor was then dipped into each sample and then allowed to dry to provide a control or "blank" comparison. Ferric chloride was then added to each sample to provide a concentration of 64 ppm of ferric ion in each sample. The comparison coatings on the tongue depressor were visually observed to provide a basis for the comparison. After 30 minutes a bluish gray discoloration formed in the paints themselves and the dry films of the painted tongue depressor.

Latex Paint Formulation Containing Sodium Pyrithione and Zinc Oxide:

| Ingredient | Grams |
| --- | --- |
| water | 240.00 |
| hydroxyethyl cellulose | 6.0 |
| Tamol 850[5] | 14.2 |
| Ethylene Glycol | 50.0 |
| Colloid 643[6] | 2.0 |
| Triton ® CF-10[7] | 5.0 |
| sodium pyrithione 40% active | 3.0 |
| potassium tripolyphosphate | 3.0 |
| Pigment grind: | |
| titanium dioxide (Rutile) | 424.0 |
| aluminum magnesium silicate | 228.0 |
| attapulgite clay | 3.0 |
| aluminum silicate | 100.0 |
| propylene glycol | 68.0 |
| Let Down: | |
| water | 84.0 |
| acrylic latex emulsion 58.0% solids | 700.0 |
| Colloid 643 | 6.0 |
| Texanol ®[8] | 18.6 |
| hydroxyethyl cellulose 2.5% in water | 236.4 |
| Total Mass in Grams | 2193.2 |

[5] An anionic dispersant, a product of Rohm and Haas Company
[6] A defoamer, a product of Rhone-Poulence Corp.
[7] A nonionic surfactant, a product of Union Carbide Corp.
[8] A coalescent, a product of Eastman Kodak Company

EXAMPLE 2

Elimination of Blue Discoloration Caused by the Presence of Pyrithione and Ferric Ion In a Paint Efficacy of zinc oxide in eliminating blue coloration caused by the presence of ferric ion in zinc pyrithione containing paint.

In the presence of ferric ion, zinc pyrithione-containing paint compositions also tended to turn blue to gray, although at a much slower rate than did the sodium pyrithione-containing paints.

48 percent aqueous zinc pyrithione was added to a white paint which contained 1.0 percent zinc oxide to provide a level of 3000 ppm of zinc pyrithione in the sample. Ferric chloride was then added to provide a concentration of 64 ppm of ferric ion in the sample. Upon standing for a month, the paint was found to have no discoloration.

When this composition is painted over bare steel or copper, no discoloration is detected. This result is surprising, since the copper would have been expected to turn the paint a greenish color, and the steel would have been expected to turn the paint a bluish color.

As a comparison, 48 percent aqueous zinc pyrithione is added to a white paint containing no zinc oxide to provide a level of 3000 ppm of zinc pyrithione in the sample. Ferric chloride is then added to provide a concentration of 64 ppm of ferric ion in the sample. Upon standing for a week, the paint is found to turn bluish in color.

EXAMPLE 3

Process for the Removal of Discoloration Caused by the Presence of Pyrithione and Ferric Ion in Water-based Coatings 48 percent aqueous zinc pyrithione was added to a white paint sample to provide a level of 3000 ppm of zinc pyrithione in the sample. Ferric chloride was then added to provide a concentration of 25 ppm of ferric ion in the sample. Upon standing for two days, the paint was found to turn bluish in color. To this point 0.007 percent (70 ppm) of zinc sulfate was added and the paint was mixed for 5 minutes. After sitting for an additional 5 minutes it was observed that the paint had whitened and the bluish color was no longer noticeable. The addition of the zinc sulfate to this paint had removed the blue color which was formed from the addition of zinc pyrithione and ferric chloride.

What is claimed is:

1. An aqueous antimicrobial composition, protected against discoloration attributable to the presence of ferric ion or cupric ion therein, said composition being selected from the group consisting of water-based paints, adhesives, caulks and sealants, and combinations thereof, said composition comprising water, pyrithione, zinc ion and a resin selected from the group consisting of vinyl, alkyd, epoxy, acrylic, polyurethane, polyester, and combinations thereof, said zinc ion being present in said composition in an amount of between 10 ppm and 90 ppm.

2. The composition of claim 1 wherein said zinc ion is present in said composition in an amount of between 10 ppm and 70 ppm.

3. An aqueous antimicrobial composition, protected against discoloration attributable to the presence of ferric ion or cupric ion therein, said composition being selected from the group consisting of water-based paints, adhesives, caulks and sealants, and combinations thereof, said composition comprising water, pyrithione, a resin selected from the group consisting of vinyl, alkyd epoxy, acrylic, polyurethane, polyester, and combinations thereof, and a zinc compound selected from the group consisting of zinc salts of organic acids, zinc salts of inorganic acids, zinc hydroxide, zinc oxide, and combinations thereof, said zinc compound being present in said composition in an amount of between 0.001% to 10% based upon the weight of the aqueous composition.

* * * * *